(12) United States Patent
Bauer

(10) Patent No.: US 7,896,798 B2
(45) Date of Patent: Mar. 1, 2011

(54) IMPLANT FOR TREATMENT OF MALE URINARY STRESS INCONTINENCE

(75) Inventor: Wilhelm Bauer, Vienna (AT)

(73) Assignee: AMI Agency for Medical Innovations GmbH, Feldkirch (AT)

( * ) Notice: Subject to any disclaimer, the term of this patent is extended or adjusted under 35 U.S.C. 154(b) by 733 days.

(21) Appl. No.: 11/658,890

(22) PCT Filed: Jun. 8, 2005

(86) PCT No.: PCT/AT2005/000206
§ 371 (c)(1),
(2), (4) Date: Jan. 30, 2007

(87) PCT Pub. No.: WO2006/012653
PCT Pub. Date: Feb. 9, 2006

(65) Prior Publication Data
US 2009/0227832 A1  Sep. 10, 2009

(30) Foreign Application Priority Data
Aug. 4, 2004  (AT) ................................ A 1341/2004

(51) Int. Cl.
*A61F 2/02* (2006.01)
(52) U.S. Cl. ............................................. 600/31; 600/37
(58) Field of Classification Search .............. 600/29–32, 600/37
See application file for complete search history.

(56) References Cited

U.S. PATENT DOCUMENTS

| | | | | |
|---|---|---|---|---|
| 4,584,990 A | * | 4/1986 | Haber et al. ..................... 600/31 |
| 4,592,339 A | * | 6/1986 | Kuzmak et al. ............... 128/899 |
| 5,934,283 A | | 8/1999 | Willem et al. | |
| 6,042,534 A | * | 3/2000 | Gellman et al. ................. 600/30 |
| 6,786,861 B1 | | 9/2004 | Pretorius | |
| 7,198,597 B2 | * | 4/2007 | Siegel et al. .................... 600/30 |

(Continued)

FOREIGN PATENT DOCUMENTS

DE  101 38 950  2/2003

(Continued)

OTHER PUBLICATIONS

Written Opinion of the International Searching Authority mailed Aug. 26, 2005 for International Application No. PCT/AT2005/000206.

(Continued)

*Primary Examiner* — Charles A Marmor, II
*Assistant Examiner* — Carrie Dorna
(74) *Attorney, Agent, or Firm* — Wenderoth, Lind & Ponack, L.L.P.

(57) ABSTRACT

An implant for treating male urinary stress incontinence includes a tape (1), and a cushion (5) capable of being filled with fluid, which tape (1) with the cushion (5), when laid onto the patient's urethra, may be looped over the lower pubic branch and may be surgically fixed under tension. For creating such an implant, which may be implanted also without anchoring on the pelvis (8) and which allows for an optimum treatment, it is provided that the tape (1) includes a broadened region (2), to which region (2) the free ends (3) of the tape (1), when implanted, after the loop-over, may be fixed, and in that the cushion (5) is arranged in the region (2), which cushion (5) is connected with a duct (6), which extends outside the tape (1), for supplying and removing the fluid.

26 Claims, 3 Drawing Sheets

U.S. PATENT DOCUMENTS

2003/0216814 A1 11/2003 Siegel et al.
2004/0215054 A1* 10/2004 Siegel et al. .................... 600/31
2005/0027160 A1 2/2005 Siegel et al.

FOREIGN PATENT DOCUMENTS

| WO | 00/18319 | 4/2000 |
|---|---|---|
| WO | 03/094784 | 11/2003 |

OTHER PUBLICATIONS

International Search Report mailed Aug. 26, 2005 for International Application No. PCT/AT2005/000206.

* cited by examiner

IMPLANT FOR TREATMENT OF MALE URINARY STRESS INCONTINENCE

The invention relates to an implant for the treatment of male urinary stress incontinence, comprising a tape and a cushion, which may be filled with fluid, which tape, when laid with the cushion onto the patient's urethra, may be looped over the lower pubic branch und may be surgically fixed under tension.

Urinary incontinence is a common disease in men and women, in particular in older persons. In men, the main causes of urinary stress incontinence are surgical interventions in the minor pelvis, in particular radical prostatectomy, and endourological interventions on the prostate and the urethra, which may lead to sphincter injuries.

The so-called stress incontinence is one form of urinary incontinence, which is characterised by involuntary passing of urine under physical stress. In the early stage of the disease improvements may be achieved by conservative measures, such as, e.g., gymnastics for strengthening the pelvic floor or biofeedback and electrostimulation. With a more high-grade incontinence a surgical treatment is necessary.

The most common surgical treatment of urinary stress incontinence in women includes an implantation of a so-called "TVT" ("tension-free vaginal tape"), which is looped over the rear part of the urethra and the free ends of which are fixed on the inner side of the abdominal wall above the pubic bone. In doing so, the synthetic tape comes to rest below the urethra in a tension-free manner and, under loads, such as coughing and sneezing, it prevents the urethra from lowering, thus sealing the same.

WO 02/02031 A1 shows, e.g., such an implant for treating urinary stress incontinence in females.

DE 101 03 179 A1 also describes a device for treating urinary stress incontinence in women, comprising a strip for supporting the urethra.

DE 101 38 950 A1 describes a TVT for treating urinary incontinence, in particular in women, which is designed to be flexible and which at least partly consists of absorbable material. Said tape comprises a chamber fillable with fluid. Said tape is arranged below the urethra in a tension-free manner and the free ends of the tape are anchored in the abdominal wall by ingrowing connective tissue. Said tape is not suitable for treating male urinary incontinence already for biomechanical and anatomical reasons.

Besides the above-mentioned TVTs so-called "TOTs" (TOT—transobturator tape sling" or transobturatory tapes are also used in surgical therapy of urinary stress incontinence in women.

US 2003/0212305 A1 describes an implantation tool and an implantation method for treating incontinence in women with the above-mentioned transobturatory system.

Implants for treating female urinary incontinence are also known for supporting the bladder, as, e.g., according to U.S. Pat. No. 5,840,011 A.

Such tension-free implants are not suited for the use in males due to the different anatomical facts.

Currently, tapes provided with bone anchors are available for the therapy of male urinary stress incontinence, in order to be able to exert a sufficiently high pressure on the urethra. In doing so, a tape supporting the urethra is fixed on the pelvic bone and thus, an effective pressure on the urethra is achieved during stress situations. Usually, the fixing of the tape on the pelvic bone is done by means of miniature screws and bone anchors, respectively, which are mostly made of titanium. The fixing elements anchored in the bone require a more complex surgical intervention and, additionally, they are foreign bodies which may lead to rejection reactions and problems.

U.S. Pat. No. 5,163,897 A describes an implant for treating male urinary stress incontinence, wherein an inflatable balloon is placed along the urethra and is fastened on the cavernous body by corresponding claw-like elements. The balloon is connected with a hand pump via a duct, which pump is located in the scrotum. The balloon may be blown up by actuating the hand pump, so that a corresponding pressure is exerted on the urethra, sealing the latter. For voiding of the bladder, the balloon has to be emptied by actuating a corresponding valve, so as to stop the pressure on the urethra and to thus allow the urine to pass through. Beside the relatively high complexity of the implant and the high expenditure of implanting, said system requires the active participation of the patient, leading to problems, in particular in the case of older patients.

The object of the present invention is to create one of the above-mentioned implants, which can be used for the effective treatment of male urinary stress incontinence and which can be implanted in a manner as simple as possible and without side effects. The implant shall be constructed in a way as simple and as cost-effective as possible and shall produce as few rejection reactions as possible. The disadvantages of known implants shall be avoided or reduced, respectively.

The object of the present invention is achieved in that the tape has a broadened region, wherein the free ends of the tape, when being implanted, after the loop-over, may be fixed to said region, and in that the cushion is arranged in said region, which cushion is connected with a duct, which extends outside the tape, for supplying and removing the fluid. The tape with the broadened region and the cushion is surgically implanted so that the cushion exerts a corresponding pressure on the urethra via the broadened region of the tape, which pressure is just as high as to prevent urine escape when under stress, e.g. when coughing or sneezing. In contrast thereto, the pressure can be adjusted individually via the cushion so as to enable voiding of the bladder by the patient without actuating the implant or taking other measures. Via the broadened region of the tape, a pressure is exerted on the urethra over a longer section of the latter. No urethra injuries can result due to the pressure distribution over the broadened region. The inventive implant does not require a fixing on the pelvic bone but is placed in the desired position by laying onto the urethra and passing the free ends of the tape through the openings in the pelvic bone, and a permanent fixing on the pelvis is achieved by fixing the ends of the tape on the broadened region. Rejection reactions and surgical complications are avoided, as fixing elements on the pelvic bone are omitted. Furthermore, the implantation can be done more easily and more quickly and thus with less strain on the patient. The arrangement of the cushion allows for the present implant to be optimally adjustable to the respective conditions by filling the cushion with fluid to exert a higher pressure on the urethra or by removing a certain amount of fluid from the cushion to reduce the pressure on the urethra. The cushion can be adjusted also particularly simply and quickly after implantation by filling the cushion or sucking-off the fluid via the skin. In order to facilitate the subsequent filling of the cushion with fluid or the sucking fluid off the cushion, the cushion may be connected with a duct which extends outside the tape. The duct is placed, e.g., in the patient's scrotum and can be palpated easily by the attending physician and consequently, the fluid can be introduced into the cushion or sucked off the cushion by piercing the skin and the duct. Thus, a subsequent correction of the pressure on the urethra can be done at any time to obtain optimum treating results. The described implant for treating male urinary stress incontinence does not need any screws and is designed to be self-supporting.

Advantageously, the broadened region of the tape is arranged substantially in the longitudinal center of the tape. The length of the tape is selected such that it can be looped over the pelvic bone once according to the anatomical conditions and then, the free ends of the tape can be fixed on the broadened region, which adjoins the urethra, e.g., by suturation or by glueing. The ends of the tape can be cut off to the desired length also during implantation.

Advantageously, the cushion fillable with fluid is arranged on that side of the tape facing the urethra when implanted.

Preferably, the broadened region comprises at least one opening for the free end of the tape, thus facilitating the fastening of the tape.

Advantageously, the free end of the duct is closed. The duct and the free end of the duct, respectively, are provided with an advantageously thin membrane to allow for piercing with a corresponding needle as easily as possible.

To facilitate piercing of the free end of the duct, said free end can be designed to be broadened.

Advantageously, a physiological saline solution is used as fluid, which solution does not have any adverse effects on the body even in the case of a leaking cushion.

The cushion can be glued with the tape on the respective side of the broadened region. In doing so, appropriate glues are used which do not provoke any rejection reactions and which do not lose their glueing effect in a long-term implantation.

It is also possible that the cushion and the tape are produced integrally.

Advantageously, the tape is made of synthetic fabrics, in particular of a polypropylene fabric. Said materials have already shown excellent properties in other implants.

The fabric tape may be soaked in silicone.

According to a further characteristic of the invention, the cushion is made of elastic synthetic material, in particular silicone.

To facilitate fixing of the ends of the tape on the broadened region after implantation, the ends of the tape can be designed to taper.

To further facilitate the implantation, eye hooks or the like may be provided on the ends of the tape for fixing the suture.

The invention also relates to a method for implanting the implant described, which method is explained in more detail by way of the annexed drawings which show an examplary embodiment of the implant for treating male urinary stress incontinence.

DETAILED DESCRIPTION OF THE INVENTION

Figure 1:
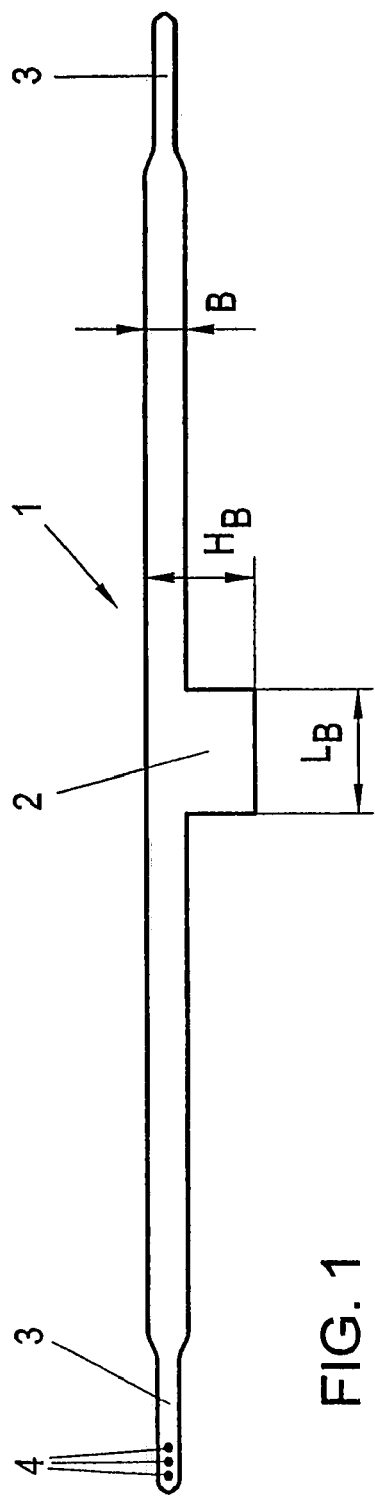
FIG. 1 shows a view on a tape in the unfolded, flat state.

FIG. 1 shows the tape 1 for the formation of the implant for treating male urinary stress incontinence, which tape comprises a broadened region 2 substantially in the longitudinal center. The free ends 3 of the tape 1 may be designed to taper. Eye hooks 4 or the like may be arranged on the free ends 3 for fixing the suture. The tape 1 preferably consists of a synthetic fabric, in particular polypropylene fabric, which may, e.g., be soaked in silicone. Said materials have good biocompatibility and are frequently used in surgery. Furthermore, such materials can be produced in a relatively cost-effective way. The dimensions of the inventive tape 1 are adapted to the respective conditions. The total length L of the tape 1 may, e.g., be in the range of between 500 and 600 mm. The broadened region 2 of the tape 1 typically comprises a length $L_B$ of 50 mm and a height $H_B$ of 40 mm. The width B of tape 1 typically is 15 mm. The tape 1 is implanted with a minimum-surgical method, in which method the urethra is exposed by a small cut and the tape 1 is installed by means of corresponding implantation tools which are used, e.g., for the implantation of transobturatory tapes for treating female urinary incontinence.

Figure 2:
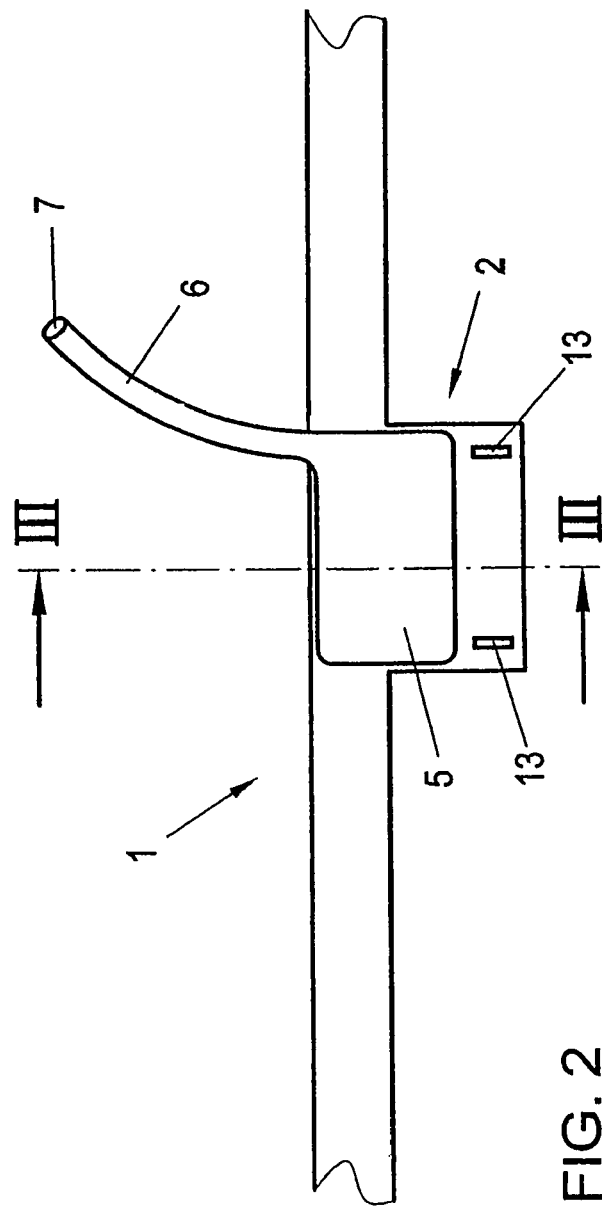
FIG. 2 shows a detailed view on the tape of FIG. 1 with the cushion being arranged thereon.
Figure 3:
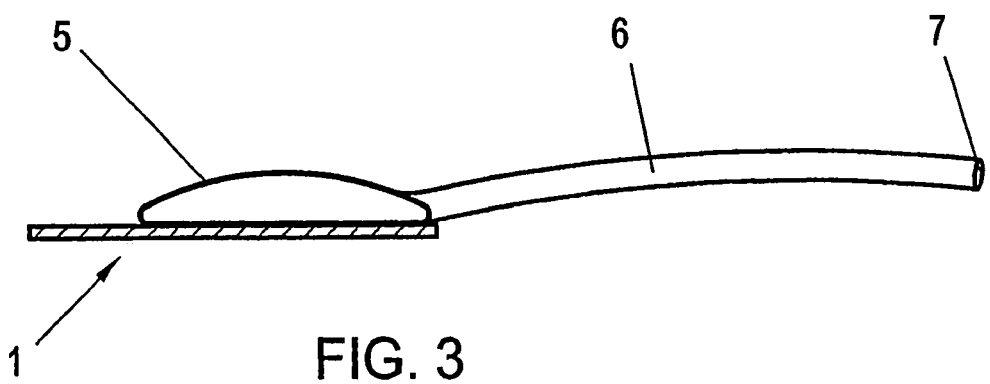
FIG. 3 shows a sectional representation through the tape of FIG. 2 along the sectional line III-III.

FIGS. 2 and 3 show a detail of the tape 1 in the area of the broadened region 2, wherein a cushion 5 is provided above at least one part of the broadened region 2, openings 13 may be provided on the broadened region (2) above which no cushion 5 is placed, in which openings the free ends 3 of the tape 1 may be inserted for a better fixing. It is also possible to arrange several interconnected cushions 5. The cushion 5 may be glued with the tape 5 or be produced integrally therewith. To facilitate a subsequent filling or emptying of the cushion 5, said cushion is connected to a duct 6, the free end 7 of which being closed to prevent an undesired escape of the fluid, in particular of the saline solution, provided in the cushion 5. The free end 7 of the duct 6 is arranged on a suitable site, e.g. in the region of the patient's scrotum. The fluid may be introduced into or sucked off, respectively, the cushion 5 by piercing the skin and the free end 7 of the duct 6 by means of a needle.

Figure 4:
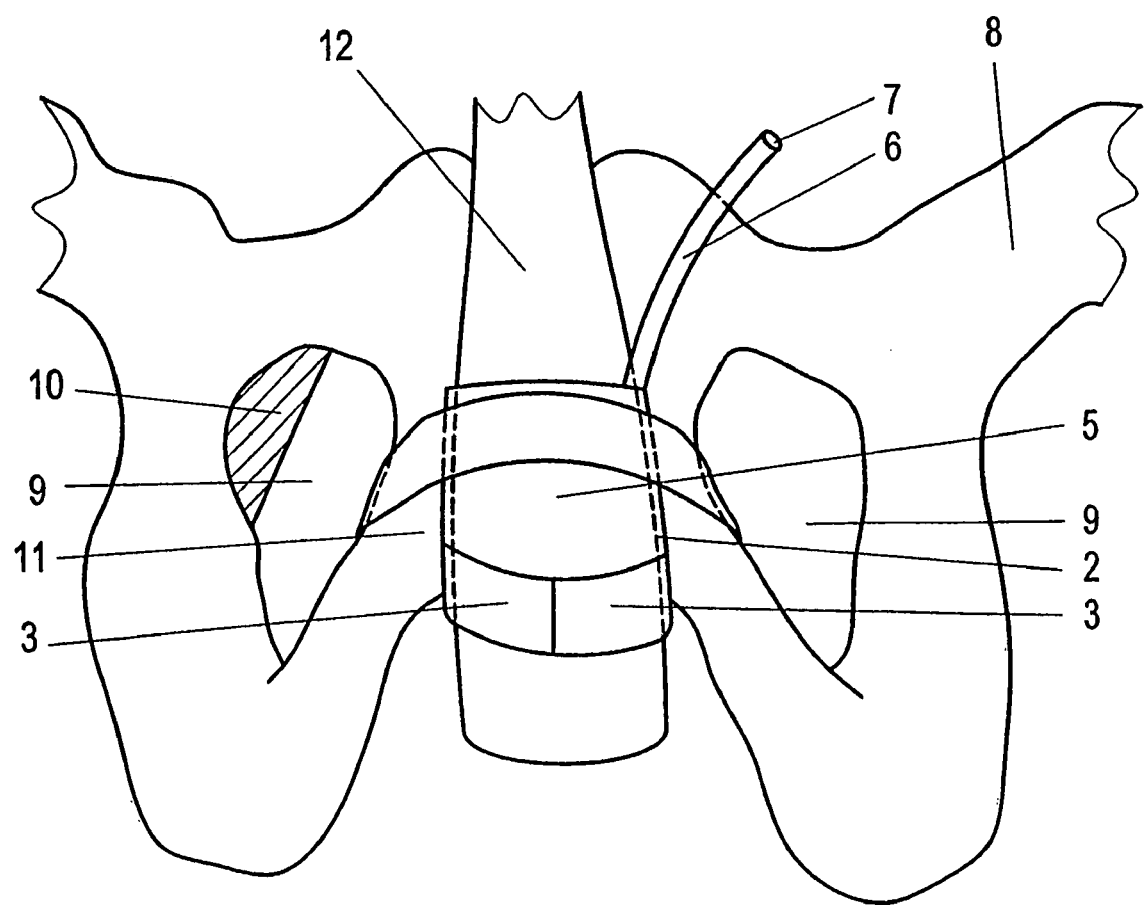
FIG. 4 schematically shows the view from the bottom on the implant fastened to the pelvis after implantation.
Figure 5:
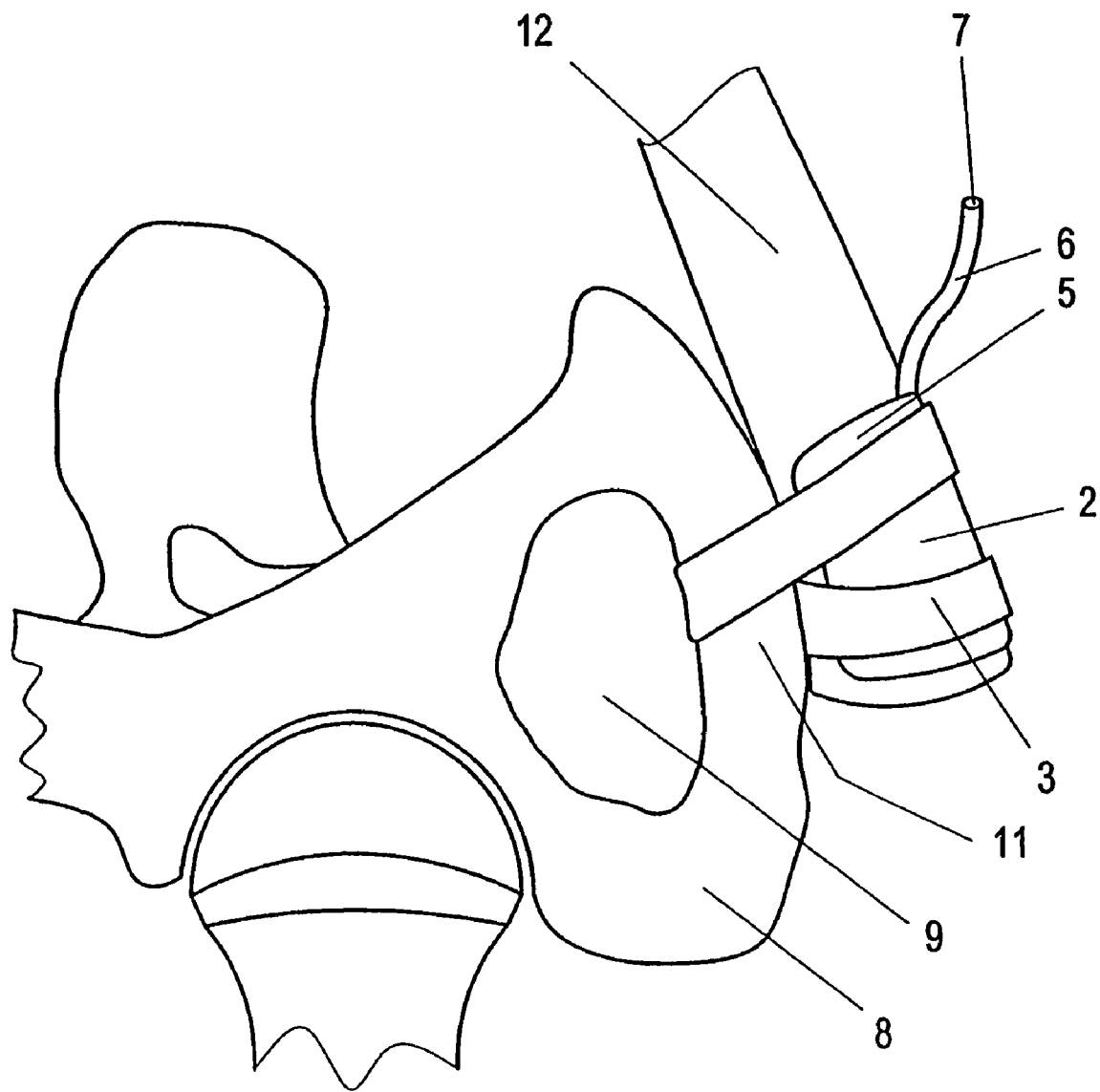
FIG. 5 shows the implant fastened to the pelvis in a side view.

FIG. 4 shows a view on the implant fastened to the pelvis 8 after said implantation. The implantation can be done under spinal anaesthesia or general anaesthesia. In supine position, the patient is perineally placed. A vertical perineal cut of about 5 cm in length is made shortly below the scrotum. Then, the urethra and the musculus bulbospongiosus lying thereabove are demonstrated. On this structure 12, on both sides laterally, the lower pubic branch 11 (ramus inferior ossis pubis) is demonstrated. As anatomical structures, starting laterally, there are the ramus inferior ossis pubis 11, the crus of the Corpus cavernosus, and the urethra with the Musculus bulbospongiosus abutting medially, which is preserved (structure 12). Subsequently, a small incision of the pelvic fascie is made about 2 cm below the symphysis on both sides by means of the scissors, laterally of the crus and medially of the ramus inferior ossis pubis 11. By this incision, a helical trocar, similar to that described in patent WO 02/02031 A1, is led around the ramus inferior ossis pubis 11. By this, the membrana obturatoria close to the ramus inferior ossis pubis 11 is perforated on the contralateral side of the course of the nervus obturatorius in the region 10 of the opening 9 (the foramen obturatorium) of the pelvis 8. In doing so, the dangerous region 10 of the openings 9 in pelvis 8, in which nerves and blood vessels extend, is not affected, whereby the risk of surgery and the risk of a hemorrhage can be reduced. In contrast to the conventional technique of implanting in women, the trocar is led in a so-called inside-out technique, and the skin is not pierced, but, arriving from dorsal, the trocar is guided at the ventral side of the ramus inferior ossis pubis 11 to the perineal site of incision. By the eye hook in the trocar, one end of the tape 1 is fixed, and the trocar is retracted in a helical movement which is predetermined by the curvature. The same way of implanting also occurs at the other side.

Due to this way of implanting, the cushion 5 arranged in the middle of the tape 1 in the broadened region 2 thereof comes to lie in front of the urethra in the structure 12 at the level of the symphysis. The ends of the loop are now fixed to the lower part of the broadened range 2 of the tape 1 by suturing or by gluing. By filling the cushion 5 and simultaneously retrograde measuring of the urethral closure pressure, the optimum pressure on the urethra in the structure 12 is adjusted. For filling the cushion 5, the free end 7 of the duct 6 subsequently is laid into a small surgically provided pocket in the scrotum. Then the wound is closed, layer by layer.

Fastening of the implant thus occurs without anchoring on the lower pubic branch 11 of the pelvis 8, facilitating surgery and minimizing the risks. During implantation, the pressure on the urethra in structure 12 is achieved by an appropriate fastening of the free end 3 of tape 1 and by supplying or discharging fluid into and out from cushion 5. By filling cushion 5 via duct 6, or the free end 7 of duct 6, respectively, an appropriate pressure is exerted on the urethra which ensures sealing of the latter during stress, such as coughing and sneezing, and, nevertheless, allows for an intentional voiding of the bladder. As described above, this desired pressure is measured during surgery and adjusted by appropriately filling the cushion 5. Later on, an adaptation, e.g. to a changed situation, may be effected at any time in an outpatient department without great effort by filling or emptying the cushion 5 via duct 6.

The present invention exhibits a new transobturatory system for treating male urinary stress incontinence which does not require screws for anchoring on the pelvis. The implant is designed to be self-supporting and can be adjusted individually by integration of the cushion.

The invention claimed is:

1. An implant for treating male urinary stress incontinence, comprising:
    a tape having a broadened region, the broadened region having at least one opening;
    a cushion capable of being filled with fluid, the cushion being arranged on a front side of the broadened region of the tape;
    a duct connected to the cushion and extending outside the tape for supplying and removing the fluid to and from the cushion; and
    means for securing the tape and the cushion, in a position in which the cushion lies on a urethra of a patient, by looping around a lower pubic branch of the patient, through the at least one opening of the broadened region and being fixed to a back side of the broadened region so as to secure the tape and the cushion under tension without completely surrounding the urethra.

2. The implant according to claim 1, wherein the broadened region is arranged substantially in a longitudinal center of the tape.

3. A method comprising:
    providing the implant as recited in claim 2;
    making at least one incision in a patient;
    forming an insertion path for the implant;
    fixing the implant so as to support the urethra; and
    closing the at least one incision.

4. The implant according to claim 1, wherein a free end of the duct is closed.

5. The implant according to claim 4, wherein the free end of the duct is designed to be broadened.

6. A method comprising:
    providing the implant as recited in claim 5;
    making at least one incision in a patient;
    forming an insertion path for the implant;
    fixing the implant so as to support the urethra; and
    closing the at least one incision.

7. A method comprising:
    providing the implant as recited in claim 4;
    making at least one incision in a patient;
    forming an insertion path for the implant;
    fixing the implant so as to support the urethra; and
    closing the at least one incision.

8. The implant according to claim 1, wherein the fluid comprises saline solution.

9. A method comprising:
    providing the implant as recited in claim 8;
    making at least one incision in a patient;
    forming an insertion path for the implant;
    fixing the implant so as to support the urethra; and
    closing the at least one incision.

10. The implant according to claim 1, wherein the cushion is glued to the tape.

11. A method comprising:
    providing the implant as recited in claim 10;
    making at least one incision in a patient;
    forming an insertion path for the implant;
    fixing the implant so as to support the urethra; and
    closing the at least one incision.

12. The implant according to claim 1, wherein the cushion and the tape are produced integrally.

13. A method comprising:
    providing the implant as recited in claim 12;
    making at least one incision in a patient;
    forming an insertion path for the implant;
    fixing the implant so as to support the urethra; and
    closing the at least one incision.

14. The implant according to claim 1, wherein the tape comprises a synthetic fabric.

15. The implant according to claim 14, wherein the tape comprises a polypropylene fabric.

16. The implant according to claim 14, wherein the tape is soaked in silicone.

17. A method comprising:
    providing the implant as recited in claim 14;
    making at least one incision in a patient;
    forming an insertion path for the implant;
    fixing the implant so as to support the urethra; and
    closing the at least one incision.

18. The implant according to claim 1, wherein the cushion is formed of an elastic synthetic material.

19. The implant according to claim 18, wherein the cushion is formed of silicone.

20. A method comprising:
    providing the implant as recited in claim 18;
    making at least one incision in a patient;
    forming an insertion path for the implant;
    fixing the implant so as to support the urethra; and
    closing the at least one incision.

21. The implant according to claim 1, wherein ends of the tape are designed to taper.

22. A method comprising:
    providing the implant as recited in claim 21;
    making at least one incision in a patient;
    forming an insertion path for the implant;
    fixing the implant so as to support the urethra; and
    closing the at least one incision.

23. The implant according to claim 1, wherein eye hooks are provided on ends of the tape for fixing a suture.

24. A method comprising:
    providing the implant as recited in claim 23;
    making at least one incision in a patient;

forming an insertion path for the implant;
fixing the implant so as to support the urethra; and
closing the at least one incision.

25. A method comprising:
providing the implant as recited in claim 19;
making at least one incision in a patient;
forming an insertion path for the implant;
fixing the implant so as to support the urethra; and
closing the at least one incision.

26. A method of implanting an implant for treating male urinary stress incontinence, the implant including a tape having a broadened region and free ends extending outwardly from the broadened region, the broadened region having at least one opening for receiving the free ends of the tape, a cushion capable of being filled with fluid, the cushion being arranged on a front side of the broadened region of the tape, and a duct connected to the cushion and extending outside the tape for supplying and removing the fluid to and from the cushion, the method comprising:
making at least one incision in a patient;
forming an insertion path for the implant;
positioning the implant such that the cushion lies on the urethra of the patient;
looping the free ends of the tape around a lower pubic branch of the patient and through the at least one opening of the broadened region, and fixing the free ends of the tape to a back side of the broadened region so as to secure the tape and the cushion under tension without completely surrounding the urethra; and
closing the at least one incision.

* * * * *